(12) United States Patent
Cheng

(10) Patent No.: US 7,044,983 B1
(45) Date of Patent: May 16, 2006

(54) POSITIONING AND BUFFERING DEVICE FOR ARTIFICIAL KNEE JOINT

(76) Inventor: Chia Pao Cheng, P.O. Box 82-144, Taipei (TW)

( * ) Notice: Subject to any disclaimer, the term of this patent is extended or adjusted under 35 U.S.C. 154(b) by 0 days.

(21) Appl. No.: 10/625,660

(22) Filed: Jul. 24, 2003

(51) Int. Cl.
*A61F 2/64* (2006.01)
*A61F 2/68* (2006.01)

(52) U.S. Cl. ........................................... 623/46
(58) Field of Classification Search ............. 623/39–46
See application file for complete search history.

(56) References Cited

U.S. PATENT DOCUMENTS

| | | | | |
|---|---|---|---|---|
| 5,728,173 A | * | 3/1998 | Chen ............................ | 623/44 |
| 5,800,566 A | * | 9/1998 | Gramnas ...................... | 623/39 |
| 5,904,721 A | * | 5/1999 | Henry et al. .................. | 623/26 |
| 6,086,616 A | * | 7/2000 | Okuda et al. ................. | 623/44 |
| 6,117,177 A | * | 9/2000 | Chen et al. ................... | 623/44 |
| 2002/0188355 A1 | * | 12/2002 | Chen ............................ | 623/45 |
| 2003/0195637 A1 | * | 10/2003 | Shen ........................... | 623/44 |

\* cited by examiner

*Primary Examiner*—Bruce E. Snow
(74) *Attorney, Agent, or Firm*—Leong C. Lei

(57) ABSTRACT

A positioning and buffering device of a knee joint for artificial limb is disclosed. The device comprises a knee cap head, an interlinking device including two arch plates, a buffering device including an interlinking rod, an interlinking support and a hydraulic cylinder; a spring device having a spring and a spring support; and a knee cap body module. The knee cap body is used to connect to the thigh and the lower edge of the knee cap body is for connection to the shank and the leg bottom portion. By means of the interlinking rod and the linking support, when the leg is stretched or is standing, a pressure exerted changes the angle between the interlinking rod and the interlinking support such that the knee joint is at a fixed position, the shank will not bent or knee down and the buffering device will produce a buffering and shock absorbing effect.

1 Claim, 9 Drawing Sheets

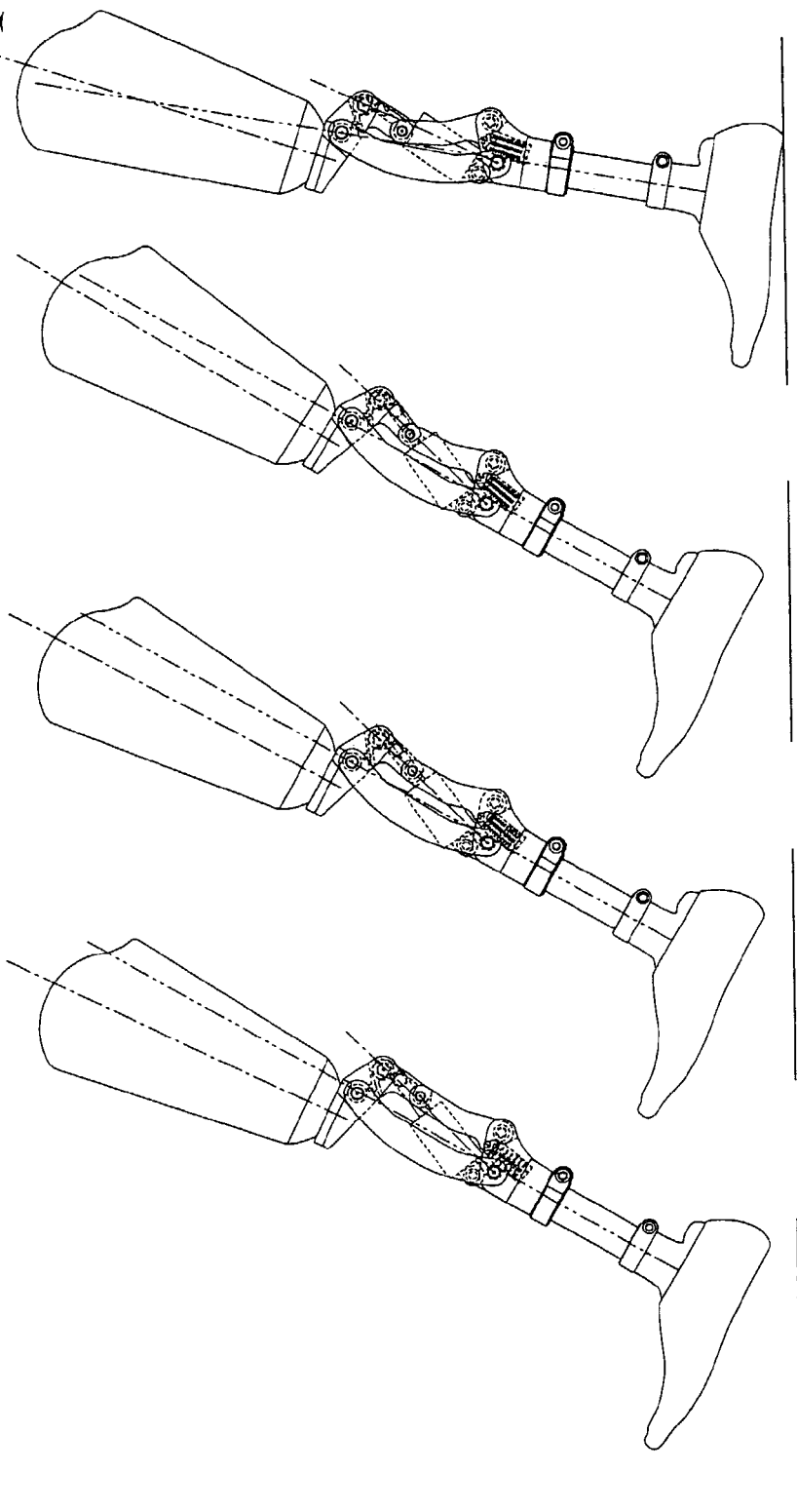

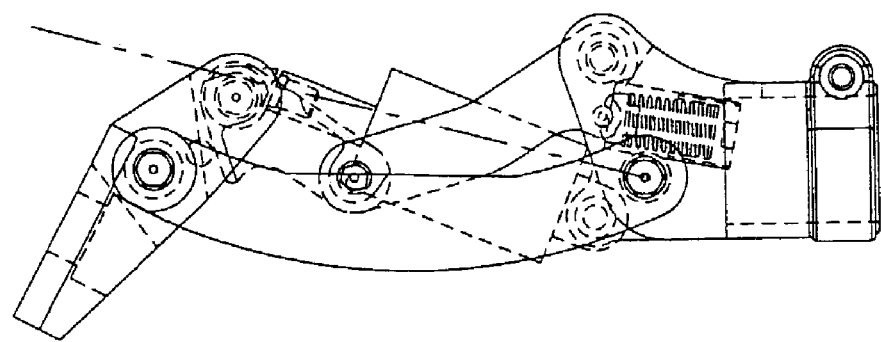
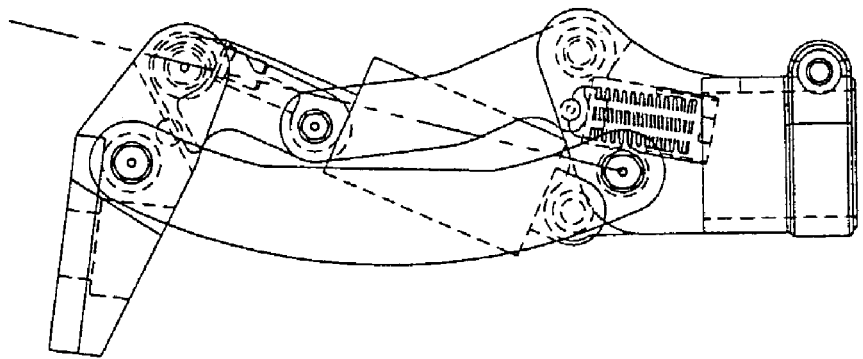
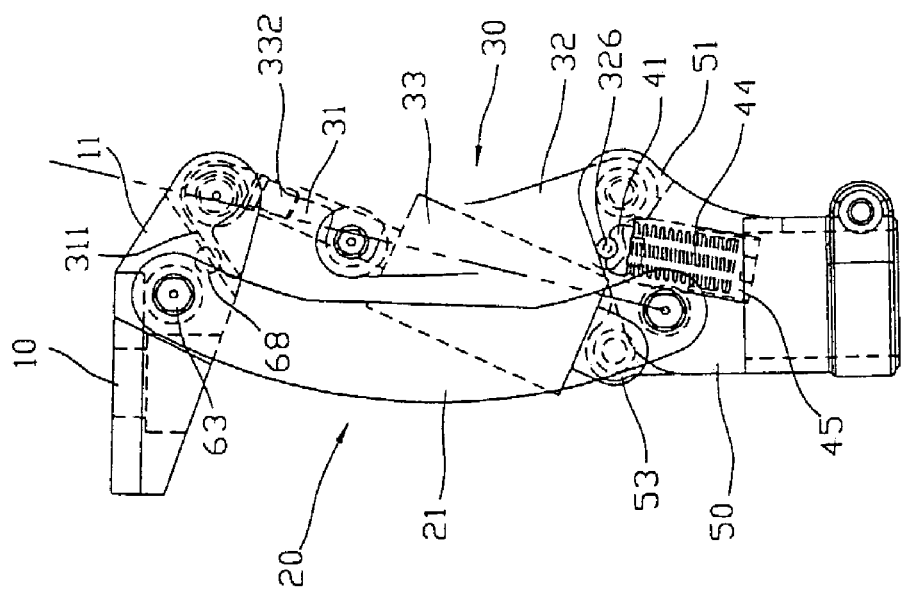

US 7,044,983 B1

POSITIONING AND BUFFERING DEVICE FOR ARTIFICIAL KNEE JOINT

BACKGROUND OF THE INVENTION (a) Technical Field of the Invention

The present invention relates to a positioning and buffering device for artificial knee joint, and in particular, to a device provided with interlinking rod and support, in the course of the moving of the knee joint within a predetermined angle, absorbing impact force exerted onto the knee joint.

(b) Description of the Prior Art

Artificial limbs and joints allow a disable to walk normally. These joints, for instance a knee joint, have an interlinking rod mounted with a pad. When the knee joint is stretched to touch the ground an impact force is exerted. This will press the pad so as to absorb the impact. However the absorbing of shock is a straight line direction of the leg portion and the knee joint, and when walking along a flat ground, the leg can be stretched straight to allow the impact force to be absorbed. However, when walking down a sloping ground, a small angle is formed and the absorbing of impact force cannot be effected. This is due to the fact that the interlinking rod cannot be positioned. When walking down hill or down a sloping ground, the interlinking rod of the knee joint bends suddenly or knees dangerously, and therefore it is not convenient for the disable to walk down hill or down a slope. Accordingly, it is an object of the present invention to provide a positioning and buffering device for artificial knee joint which mitigates the above drawback.

SUMMARY OF THE INVENTION

Accordingly, it is an object of the present invention to provide a positioning and buffering device for knee joint of an artificial limb, comprising a knee cap head, an interlinking device including two arch plates, a buffering device, a spring device and a knee cap body module, characterized in that the knee cap head is connected to the thigh, and the lower edge of the knee cap body is for the connection to the limb and the leg bottom; the buffering device includes an interlinking rod, an interlinking support and hydraulic cylinder and the spring device includes a spring and a spring support, the interlinking rod is connected to a recess within the knee cap head and an elastic block is placed within the recess such that the piston rod of the hydraulic cylinder is mounted at a recess of the interlinking rod and a needle shaft and a spindle are used for mounting, the through hole of the interlinking rod are provided with two protruded lugs of the interlinking support and are positioned using a needle shaft or screw such that the through hole at the lower section of the hydraulic cylinder and the through hole at the interlinking support housing are positioned by a spindle, the through hole at the lower section of the hydraulic cylinder with the through hole at one side of the knee cap head allow the interlinking support to hold, and two arch plates are used to fasten the knee cap head and are positioned using the screw nuts, the lower edge of the housing for the interlinking support is provided with a block body having screw holes mounted with a buffering block, and is positioned to a flat board near to the knee cap body, and the lower edge of the knee cap body is connected to the shank and the recess of the leg bottom having mounted with the spring device, the recess of the spring support is connected to the rounded portion of the interlinking support and the protruded pillar at the lower section of the spring is mounted to a spring and fastened with an adjustable screw.

Yet another object of the present invention is to provide a positioning and buffering device for artificial knee joint, wherein when the knee joint is bent backward or standing, a pressure exerted to change the interlinking rod and the angle of the interlinking rod such that the knee joint is at a positioning state and the shank will not bend or at a risky position.

A further object of the present invention is to provide a positioning and buffering device for artificial knee joint, wherein when walking on a slope the knee joint can be bent at certain angle and the buffering device produces a buffering and absorbing effect.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIGS. 6A, 6B, 6C and 6D show the continuation movement of a positioning and buffering device for artificial knee joint of the present invention.

FIGS. 7A, 7B and 7C are schematic views showing the buffering effect of a positioning and buffering device for artificial knee joint of the present invention.

DETAILED DESCRIPTION OF THE PREFERRED EMBODIMENT

Figure 1:
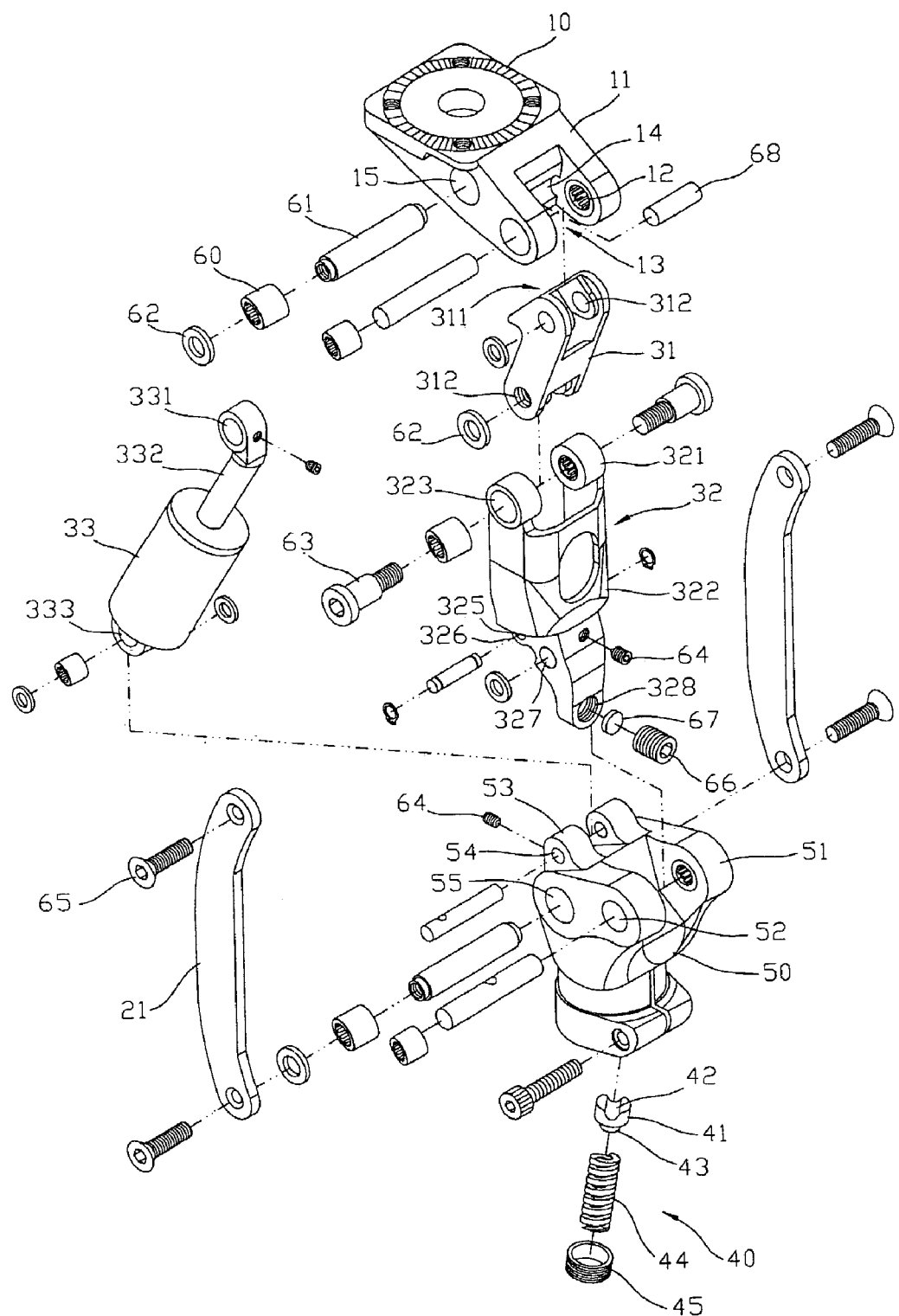
FIG. 1 is an exploded perspective view of a positioning and buffering device for artificial knee joint in accordance with the present invention.

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Referring to FIG. 1, the positioning and buffering device of an artificial knee joint comprises a knee cap head 10, an interlinking device 20 (arch plates 21), a buffering device 30 (interlinking rod 31), interlinking support 32, hydraulic cylinder 33), a spring device 40 (spring support 42, spring 44), and a knee cap body 50. The knee cap head is connected upward to the thigh and the lower edge of the knee cap body is used to connect to the shank and the leg bottom portion.

In accordance with the present invention, one side of the knee cap head 10 is extended to form two protruded wings 11 having a recess 33 and a semi arch-shaped recess 14, so that the recess 33 can hold the interlinking rod 31 of the buffering device 30. The sides of the wings 11 are provided with through holes 12, and a through hole 15 is positioned at the rear end of the wing, and the interlinking rod is corresponding to the slope 311 of the interlinking rod 31 provided at the recess of the knee cap head. In the course of urging by the interlinking rod 31 the through holes 312 at the knee cap head having a pad 62 is mounted at the recess of the knee cap head, and the arch-shaped recess has an elastic block 68 for the urging with the sloping face of the interlinking rod. The through hole is provided with needle bearing 60 and is pivotally connected with an axle 61.

Through hole 312 is provided to the block body of the interlinking rod 31 for the connection with the buffering device 30 and the protruded lug 321 at the two lateral sides of the interlinking support 32, and a housing 322 extended from the protruded lug is provided with a hydraulic cylinder 33, and the connection with the piston rod 332 is at the through hole 331. The through hole 323 provided at the side of the lug is mounted to the needle beating 60 and the through hole of the interlinking rod and that of the piston rod are in alignment such that the lugs are connected to the interlinking rod and the interlinking support with screw 63.

A block body 324 is mounted to the housing 322 at the interlinking support 32 and is sued for urging adjustment. A through hole 325 provided at the lower section of the block body for the axle 61 to pass through is made into a round section 326. The front side of the through hole is another through hole 327 mounted with the needle bearing 60 so that the wing 51 can pass through the through hole 52 and is fastened with screw 64. The through hole 333 at the lower section of the hydraulic cylinder 33 is mounted with a needle bearing 60 and is then inserted with an axle 61. A screw 64 is used for fastening. The lower section of the wing is provided with a through hole 55 to be in combination with the through hole 15 for the engagement by an axle 61. The external end of the axle 61 is mounted with a pad 62 and the left and right side of the pad 62 is mounted with the arch plate 21 of the interlinking device 20. The top and bottom end are locked with screw 65. The blocking body 324 is provided with a screw hole 328 for mounting with a shock absorbing block 67 and is locked with screw 66.

The lower end of the knee cap body 50 is provided with a buffering wing 51, an interlinking wing 53 and through hole 327. The needle bearing 60 and axle 61 are connected to the interlinking support 32, the hydraulic cylinder 33 and two arch plates 21, and the lower edge of the block body was a recess with threads for the mounting of a spring device 40 so that the recess 42 of the spring support 41 can be mounted to the round portion 326 and via the protruded pillar 43 at the spring support, a spring 44 is fastened with an adjustable screw 66.

Figure 2:
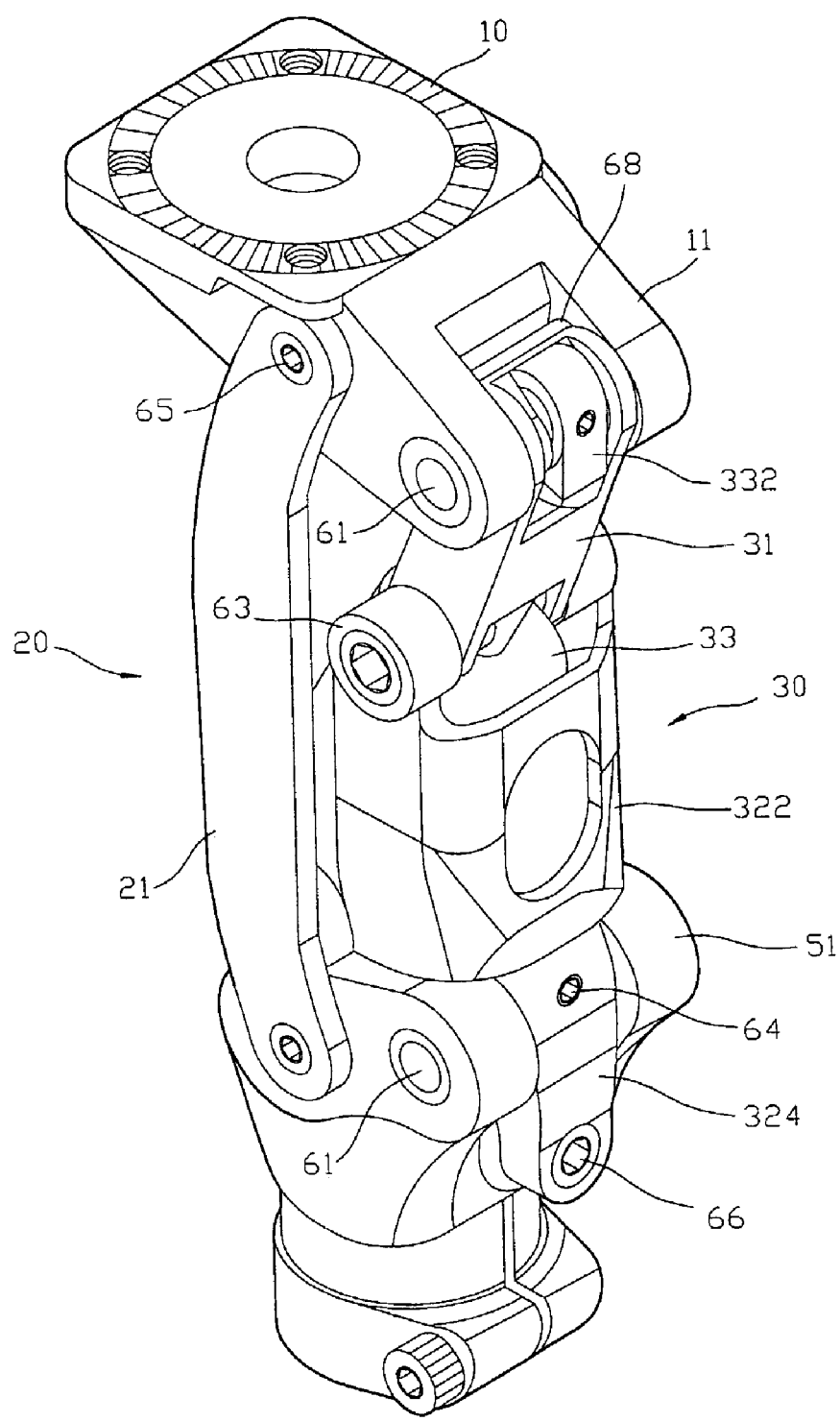
FIG. 2 is a perspective view of a positioning and buffering device for artificial knee joint of the present invention.
Figure 3:
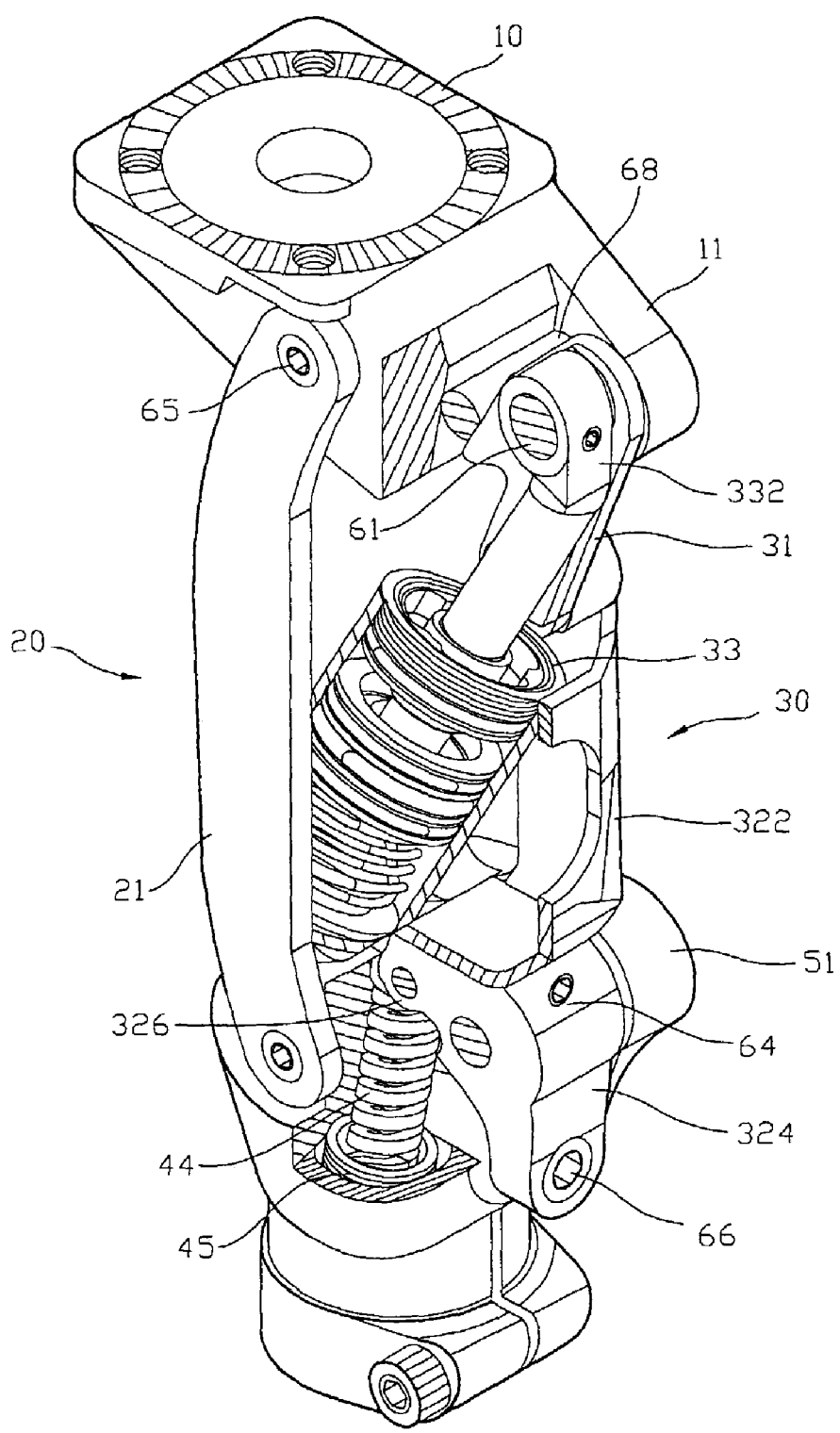
FIG. 3 is a partial sectional view of a positioning and buffering device for artificial knee joint of the present invention.
Figure 4D:
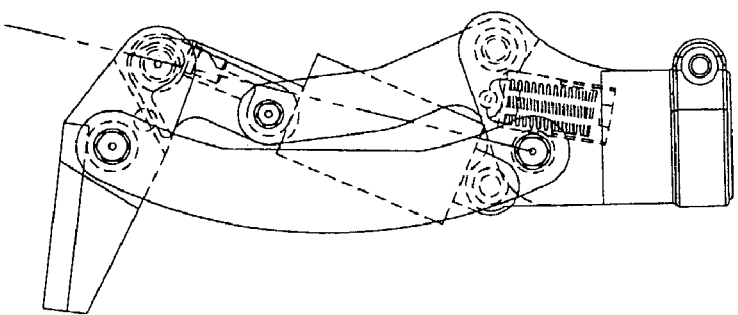
FIGS. 4A, 4B, 4C and 4D are schematic views showing the continuation movement of the positioning and buffering device for artificial knee joint of the present invention.
Figure 4C:
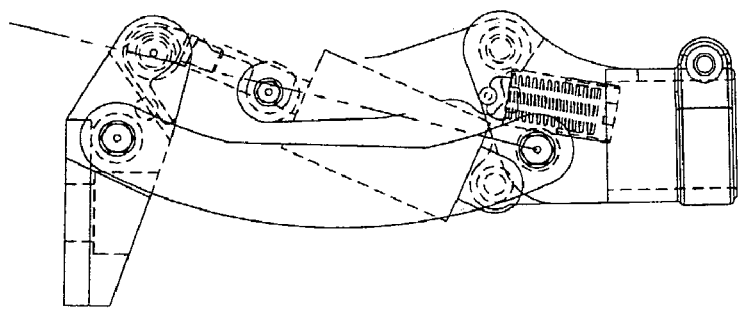
Figure 4B:
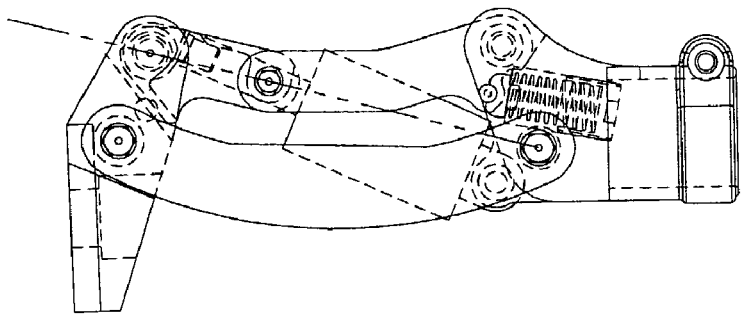
Figure 4A:
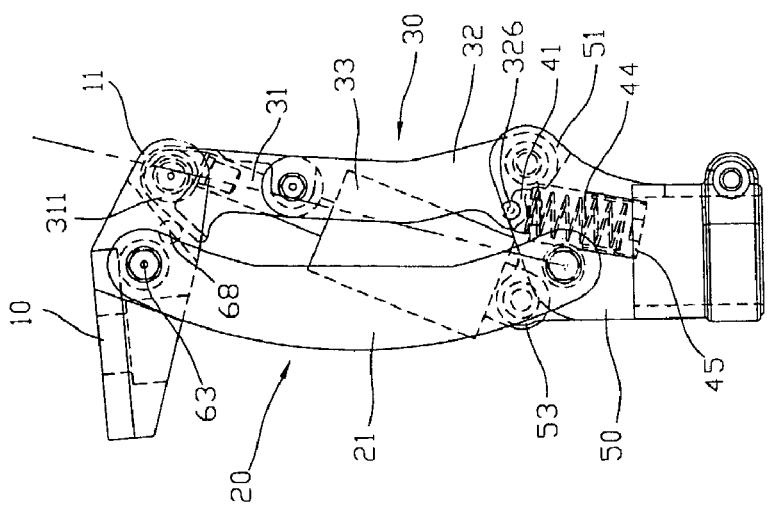

Referring to FIGS. 2 and 3, the recess 14 is provided with the elastic block 68 and the piston rod 332 is also mounted to the recess and is fastened by the needle bearing 60 and the axle 61. The lower section of the interlinking rod is provided with through hole to combine with the through hole of the protruded lug 321 and a needle bearing 60 and fastening screw 63 are used for positioning. The through holes 331 and 325 are mounted with the needle bearing 60 together with an axle 61 and is fastened by screw 64, and the through hole of the hydraulic cylinder is fastened together with the through hole 54 of the wing 53, and the through hole at the lower portion of the interlinking support is used for connection with the buffering wing 51. The through hole 327 of the knee cap head and the knee cap body after mounted with the needle bearing 60 and the axle 61 are then fastened with two arch shaped plates 21 and then fastened with screw. The lower edge or the body block is formed into recess for connection to the shank and leg bottom. The recess is threaded for mounting to a spring device 40, and the recess 42 of the spring support is in engagement with the round portion 326 of the interlinking support, and the pillar 43 is mounted with a spring 44 and is fastened by an adjusting screw 45. The screw hole 328 is mounted with a shock absorbing block 67 and a screw 66 is used for fastening so as to contact with the flat board at the buffering wing.

In the course of standing, the interlinking support is pressed and the spring is forced, which produces a buffering effect. The adjusting screw is used to change the angle of the interlinking support so as to allow easy bending and swinging. The screw can increase or reduce the spring force generated by the spring so that the pressure of the buffering is affected.

Figure 5:
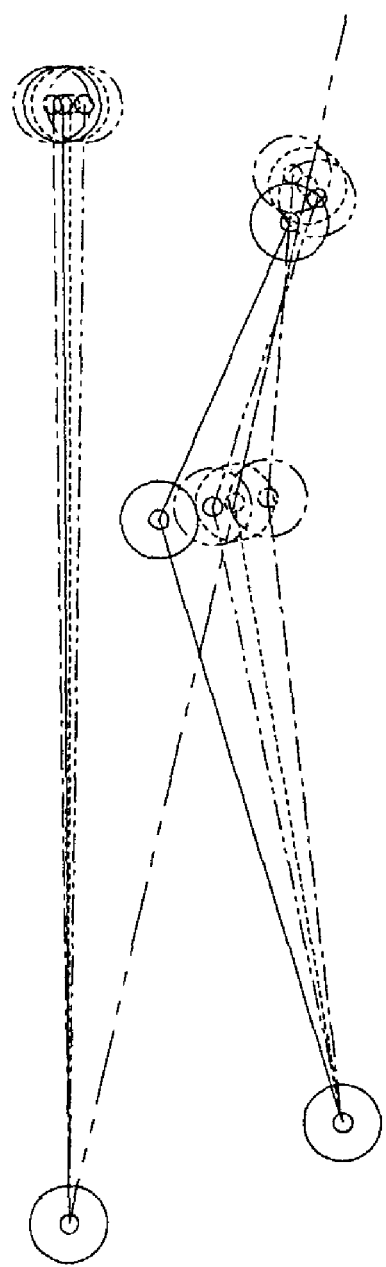
FIG. 5 is a schematic view in line presentation, showing the continuation movement of the positioning and buffering device for artificial knee joint of the present invention.

FIGS. 4 to 6 illustrate a best mode of continuation dynamic operation so as to explain the application of the steps in accordance with the present invention.

Referring to FIGS. 4 to 6, the first step is the movement of leg and is then proceeded to the second step and the third step, and further continues to forth step which is the heel landed on the ground and a buffering effect is proceeded.

When the leg moves the first step as shown, there is no downward pressure exerted onto the interlinking rod and the interlinking support as a result of the walking movement and the axis of the interlinking shaft is at the right side position of the dynamic line, and the spring of the spring device has not be compressed and proceed to the second step, the axis of the interlinking shaft is moved to the dynamic position and is in a straight line with the dynamic line and at the same time, the connected interlinking shaft and the interlinking support is compressed, the spring device is fully subjected to pressure and is proceeded to a positioning state and proceeds to step 3. The axis of the interlining shaft is moved to the left side position of the dynamic line and it changes the angle of curvature. The change of curvature is in an opposite direction to the first step and the compressed spring will slowly urge the interlinking shaft end of the support so that the interlinking shaft is secured and a buffering position is obtained. When the interlinking support moves to the forth step and let the leg to swing or stand, the pressure changes the angle between the interlinking shaft and the interlinking support such that the knee joint enters into a secured position and the lower portion of the leg will not downwardly swing or bow or at a buffering state, or the angle of the curvature of the knee joint allows the knee to walk on a sloping ground and the buffering device generates a shock absorbing effect so that it is safe to the disable using the knee joint while walking.

Figure 8A:
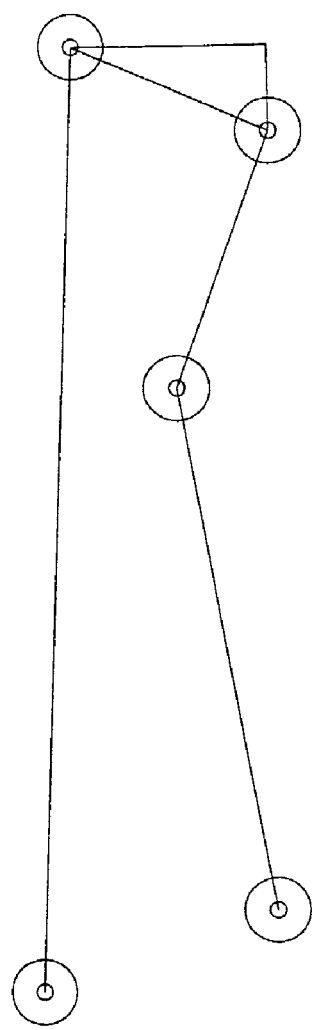
FIGS. 8A, 8B and 8C are a schematic views showing the buffering movement of a positioning and buffering device for artificial knee joint of the present invention.
Figure 8B:
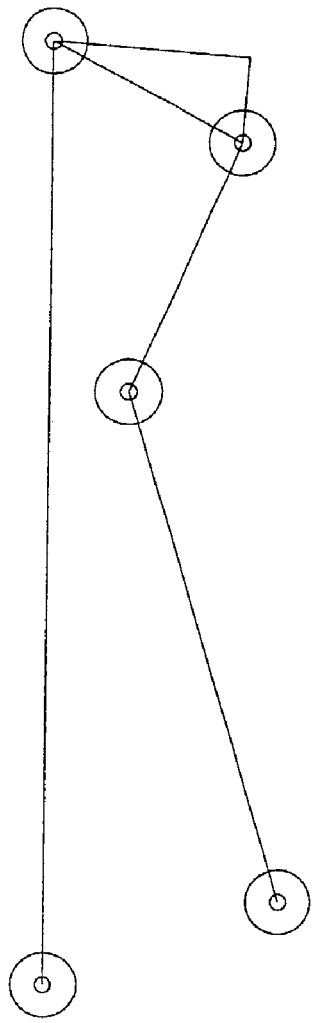
Figure 8C:
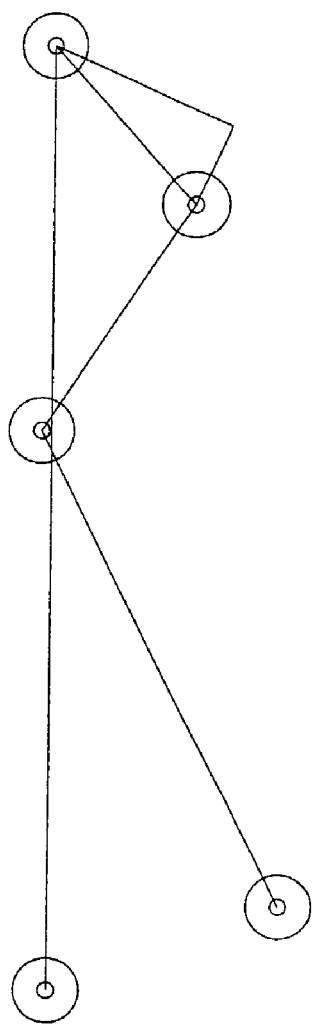
Figure 9C:
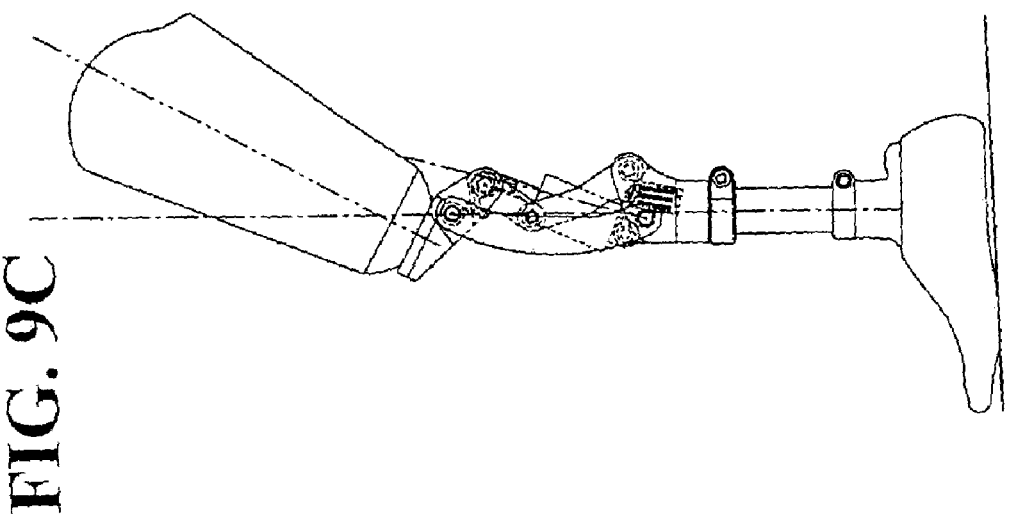
FIGS. 9A, 9B and 9C are schematic views showing the mounting of the knee joint onto an artificial limb.
Figure 9B:
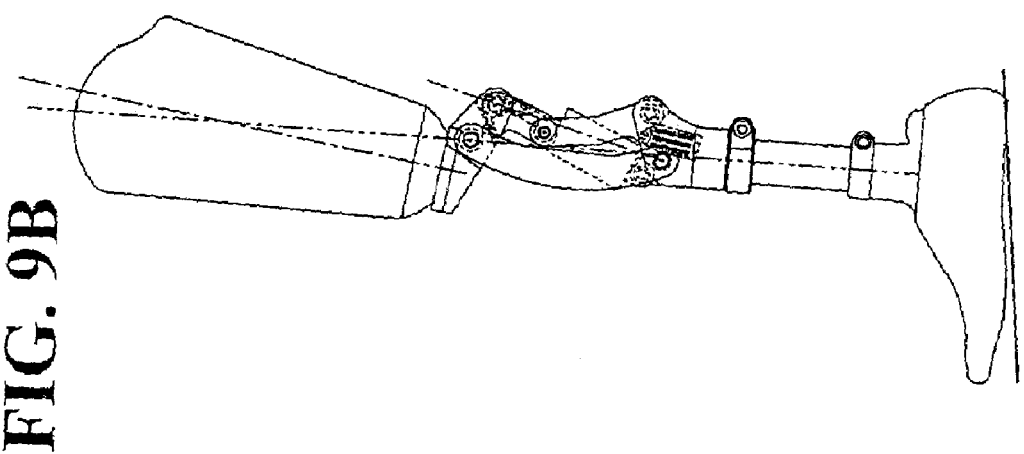
Figure 9A:
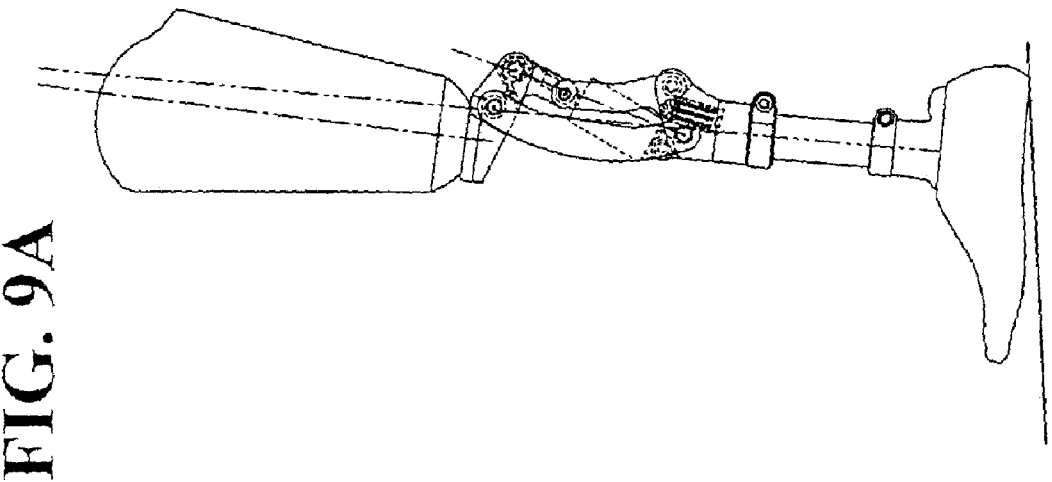

Referring to FIGS. 7 to 9, there is shown the operation of the buffering operation. As shown in steps 4 and 5, the heel moves/lands on the ground to proceed with the buffering action. In steps 5 and 6, there is shown the buffering action when walking along a slope. At this instance, the axis is biased away from the left side of the dynamic line. When the spring at the compressed spring device, the hydraulic cylinder is also compressed and a buffering effect is obtained while walking.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A positioning and buffering device for knee joint of an artificial limb, comprising a knee cap head, an interlinking device including two arch plates, a buffering device, a spring device and a knee cap body module, characterized in that the knee cap head is connectable to a thigh, and a lower edge of the knee cap body is for the connection to the limb and a leg bottom; the buffering device includes an interlinking rod, an interlinking support and hydraulic cylinder and the spring device includes a spring and a spring support, the interlinking rod is connected to a recess within the knee cap head and an elastic block is placed within the recess such that a piston rod of the hydraulic cylinder is mounted at a recess of the interlinking rod and a needle shaft and a spindle are used for mounting, a through hole of the interlinking rod is provided with two protruded lugs of the interlinking support and are positioned using a needle shaft or screw such that the through hole at a lower section of the hydraulic cylinder and the through hole at the interlinking support are positioned by a spindle, the through hole at the lower section of the hydraulic cylinder with the through hole at one side of the knee cap head allow the interlinking support to hold, and two arch plates are used to fasten the knee cap head and are positioned using the screw nuts, the lower edge of the housing for the interlinking support is provided with a block body having screw holes mounted with a buffering wing, and is positioned to a flat board near to the knee cap body, and the lower edge of the knee cap body is connected to a shank and the recess of the leg bottom having mounted with the spring device, the recess of the spring support is connected to the rounded portion of the interlinking support and a protruded pillar at the lower section of the spring is mounted to a spring and fastened with an adjustable screw.

* * * * *